(12) United States Patent
Spotnitz et al.

(10) Patent No.: US 11,260,210 B2
(45) Date of Patent: Mar. 1, 2022

(54) ULTRAVIOLET SLEEVES FOR PERCUTANEOUS DEVICES AND METHODS FOR USING AND/OR PROVIDING THE SAME

(71) Applicant: THE TRUSTEES OF COLUMBIA UNIVERSITY IN THE CITY OF NEW YORK, New York, NY (US)

(72) Inventors: Henry Spotnitz, New York, NY (US); David J. Brenner, New York, NY (US); Alan Bigelow, Hasting-On-Hudson, NY (US); Gerhard Randers-Pehrson, Ossining, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 634 days.

(21) Appl. No.: 15/574,225

(22) PCT Filed: May 16, 2016

(86) PCT No.: PCT/US2016/032755
§ 371 (c)(1),
(2) Date: Nov. 15, 2017

(87) PCT Pub. No.: WO2016/187145
PCT Pub. Date: Nov. 24, 2016

(65) Prior Publication Data
US 2018/0289940 A1 Oct. 11, 2018

Related U.S. Application Data

(60) Provisional application No. 62/162,103, filed on May 15, 2015.

(51) Int. Cl.
*A61M 39/02* (2006.01)
*A61N 5/06* (2006.01)
(Continued)

(52) U.S. Cl.
CPC ....... *A61M 39/0247* (2013.01); *A61L 2/0047* (2013.01); *A61L 2/10* (2013.01);
(Continued)

(58) Field of Classification Search
CPC .............. A61M 39/0247; A61M 1/122; A61M 2039/0285; A61M 2205/053;
(Continued)

(56) References Cited

U.S. PATENT DOCUMENTS 4,932,959 A 6/1990 Horzewski et al.
6,129,723 A * 10/2000 Anderson ............ A61C 1/0046
606/10

(Continued)

FOREIGN PATENT DOCUMENTS

WO     WO 97/09937     3/1997
WO     2012122210 A1   9/2012

OTHER PUBLICATIONS

International Search Report for International Application No. PCT/US2016/032755 dated Aug. 25, 2016.
(Continued)

*Primary Examiner* — Shirley X Jian
(74) *Attorney, Agent, or Firm* — Hunton Andrews Kurth LLP

(57) ABSTRACT

An exemplary ultraviolet (UV) arrangement, can be provided, which can include, for example, a lumen structured to be inserted into a body of a patient and pass a percutaneous structure therethrough into the body of the patient, wherein the lumen can be configured to disperse or provide a UV radiation, and an optical arrangement coupled to the lumen,
(Continued)

and configured to generate the UV radiation, and provide the UV radiation to the lumen to be dispersed or provided by the lumen. The lumen can include a weave of a plurality of strands. The optical arrangement can include an optical fiber(s) coupled to the lumen at one of the strands. The optical arrangement can include a plurality of optical fibers coupled to the lumen, where the optical arrangement can include a plurality of diffusing rings, and wherein each ring can be connected to one of the optical fibers.

17 Claims, 12 Drawing Sheets

(51) Int. Cl.
| | |
|---|---|
| *A61L 2/10* | (2006.01) |
| *A61M 60/148* | (2021.01) |
| *A61L 2/00* | (2006.01) |
| *A61L 2/26* | (2006.01) |
| *A61N 5/067* | (2006.01) |

(52) U.S. Cl.
CPC ............ *A61L 2/26* (2013.01); *A61M 60/148* (2021.01); *A61N 5/0624* (2013.01); *A61L 2202/11* (2013.01); *A61M 2039/0285* (2013.01); *A61M 2205/053* (2013.01); *A61N 5/067* (2021.08); *A61N 2005/063* (2013.01); *A61N 2005/0612* (2013.01); *A61N 2005/0651* (2013.01); *A61N 2005/0661* (2013.01)

(58) Field of Classification Search
CPC . A61L 2/0047; A61L 2/10; A61L 2/26; A61L 2202/11; A61N 5/0624; A61N 2005/0612; A61N 2005/063; A61N 2005/0651; A61N 2005/0661; A61N 2005/067
See application file for complete search history.

(56) References Cited

U.S. PATENT DOCUMENTS

| | | | |
|---|---|---|---|
| 6,551,346 | B2 | 4/2003 | Crossley |
| 8,585,627 | B2* | 11/2013 | Dacey, Jr. ............ A61L 2/0011 604/8 |
| 8,702,640 | B2* | 4/2014 | Dacey, Jr. ................ A61F 2/30 604/8 |
| 8,734,718 | B2* | 5/2014 | Dacey, Jr. ............ A61N 5/0624 422/22 |
| 8,753,304 | B2* | 6/2014 | Dacey, Jr. ................ A61L 2/00 604/8 |
| 9,259,513 | B2* | 2/2016 | Bedwell ................ A61L 2/0047 |
| 2001/0027316 | A1* | 10/2001 | Gregory ................ A61B 18/24 606/15 |
| 2003/0017073 | A1 | 1/2003 | Eckhardt et al. |
| 2003/0128944 | A1 | 7/2003 | Skutnik |
| 2008/0158629 | A1* | 7/2008 | Rheinwald ............ A61B 18/22 359/15 |
| 2009/0105597 | A1* | 4/2009 | Abraham ................ A61B 8/08 600/466 |
| 2013/0060188 | A1 | 3/2013 | Bedwell et al. |
| 2015/0126976 | A1* | 5/2015 | Tang ................ A61M 25/0012 604/544 |

OTHER PUBLICATIONS

International Written Opinion for International Application No. PCT/US2016/032755 dated Aug. 25, 2016.
Buonanno, Manuela et al., "207-nm UV Light—A Promising Tool for Safe Law-Cost Reduction of Surgical Site Infections. 1: In Vitro Studies," PLOS One, vol. 8, Issue No. 10, pp. 1-7, Oct. 2013.

\* cited by examiner

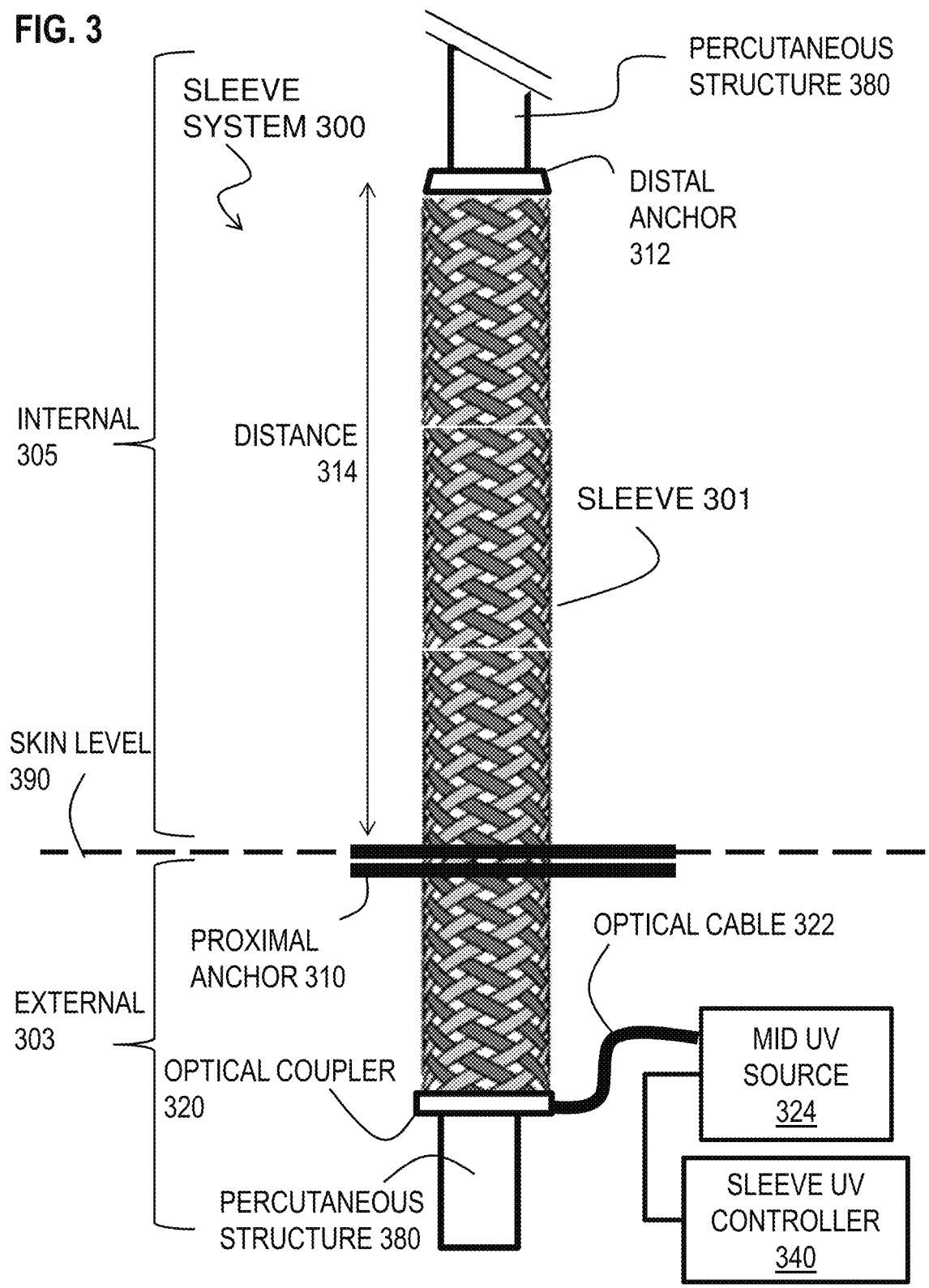

Optran PUV, Optran PWF 625
630
635
Nylon (-40° to +100°C)
ETFE (-40° to +150°C)

Optran UV, Optran WF 625
630
640
635
Polyimide (-190° to +350°C)
ETFE (-40° to +150°C)
Nylon (-40° to +100°C)
Acrylate (-40° to +85°C)

ULTRAVIOLET SLEEVES FOR PERCUTANEOUS DEVICES AND METHODS FOR USING AND/OR PROVIDING THE SAME

CROSS REFERENCE TO RELATED APPLICATIONS

This application is a national phase of and claims the benefit and priority from International Patent Application No. PCT/US2016/032755 filed on May 16, 2016, which relates to and claims the benefit of priority from U.S. Provisional Patent Application No. 62/162,103, filed on May 15, 2015, the entire disclosures of which are incorporated herein by reference.

FIELD OF THE DISCLOSURE

The present disclosure relates generally to percutaneous devices, and more specifically, to exemplary embodiments of exemplary ultraviolet sleeves for percutaneous devices.

BACKGROUND INFORMATION

Adventitious infection in medicine can affect percutaneous lines and catheters, as well as fully implanted devices and grafts. There were about 1.7 million nosocomial infections in the United States in 2002, with about 30,665 deaths due to blood stream infections and about 8,205 due to surgical site infection. All devices penetrating the human skin (e.g., percutaneous devices) are subject to infection. Infection progresses from contamination at the skin-prosthesis interface, at the penetration site. Infection is most commonly bacterial and less commonly fungal; the latter favored by antibacterial antibiotic administration. Factors affecting the probability/prevalence of infection include the following:
  Local flora at the skin surface, which varies in different areas of the human body.
  Moisture at the penetration site. This can include natural body fluids (e.g., blood, urine, lymph, bile, saliva and stool) or leaking of intravascular infusions.
  Manipulations compromising integrity of the prosthesis, for example, injection of medications into intravenous lines or changing connections.
  Surface quality of the prosthesis, including smooth, rough, woven, porous and absorptive.
  Movement of the prosthesis relative to the skin. This tends to advance materials from the external environment into the subcutaneous space.
  Adherence/ingrowth of fibrous tissue into the prosthesis, which limits movement described above.
  Local damage to the skin (e.g., burns, scrapes, cuts and chemical injury).
  Local cleansing, dressing changes and application of antibiotic ointments.
  Administration of systemic antibiotics.
  Immunocompromised state, fever or malnutrition of the host.

For example, a left ventricular assist device ("LVAD") implantation reverses end-stage heart failure, while providing a destination therapy or a bridge to cardiac transplantation. Current LVADs are dependent on percutaneous drivelines for pneumatic or electrical power. Bacterial entry along these drivelines can affect as many as about 75% of LVAD recipients, leading to antibiotic dependence, LVAD/blood stream infection and death.

Recent attempts to prevent or minimize the adventitious infection, including an impregnation with chlorhexidine-silver sulfadiazine or minocycline-rifampicin, have not eliminated the problem. Responses to the nosocomial infection threat include a prosthetic device replacement, short-term antibiotic prophylaxis and long-term antibiotic administration. These approaches are expensive and uncomfortable for, and potentially hazardous to, patients. Furthermore, overuse of antibiotics stimulates emergence of resistant bacterial strains.

Thus, it may be beneficial to provide exemplary ultraviolet sleeves for percutaneous devices, which can overcome at least some of the deficiencies described herein above.

SUMMARY OF EXEMPLARY EMBODIMENTS

An exemplary ultraviolet (UV) arrangement, can be provided, which can include, for example, a lumen structured to be inserted into a body of a patient and pass a percutaneous structure therethrough into the body of the patient, wherein the lumen can be configured to disperse or provide a UV radiation, and an optical arrangement coupled to the lumen, and configured to generate the UV radiation, and provide the UV radiation to the lumen to be dispersed or provided by the lumen. The lumen can include a weave of a plurality of strands. The optical arrangement can include an optical fiber(s) coupled to the lumen at one of the strands. The optical arrangement can include a plurality of optical fibers coupled to the lumen, where the optical arrangement can include a plurality of diffusing rings, and wherein each ring can be connected to one of the optical fibers.

In some exemplary embodiments of the present disclosure, the lumen can be separated from the percutaneous structure. The percutaneous structure can be integrated into the lumen. The percutaneous structure can be a driveline for a left ventricular assist device. A power level of the UV radiation can be at least about 0.04 milliWatts per centimeter squared of an area of an outer surface of the lumen. An outside surface of the lumen can be composed of Teflon. The optical arrangement can include a laser(s). A portable power source(s) can be configured to power the optical arrangement or the percutaneous structure. An anchor can be included, which can be configured to attach the lumen to a skin of the patient, or to attach the lumen to the percutaneous structure. A wavelength of the UV radiation can be in range of about 190 nanometers to about 230 nanometers.

A further exemplary embodiment can include a method for preventing infection of a patient, which can include, inserting a lumen into a body of the patient, generating an ultraviolet (UV) radiation, providing the UV radiation to the lumen, and irradiating the patient using the UV radiation provided to the lumen. A wavelength of the UV radiation can be in a range of about 190 nanometers to about 230 nanometers. A percutaneous structure can be inserted through the lumen into the body of the patient. The lumen can include a weave of a plurality of strands. The UV radiation can be generated using a laser.

In certain exemplary embodiments of the present disclosure, devices and techniques can be provided for applying a sleeve around a percutaneous structure, in which the sleeve can introduce ultraviolet ("UV") light at one or more wavelengths in a range from about 190 nanometers (e.g., nm, 1 nm=10-9 meters) to about 230 nm, and particularly in a range from about 207 nm to about 222 nm, to remediate the mechanisms of adventitious infection. Longer wavelengths can be omitted to avoid damage to the cells of the subject into which the percutaneous device can be implanted.

Shorter wavelengths can be omitted because such UV radiation can be very efficiently absorbed by oxygen, producing ozone and oxidative damage to human cells. Because the UV wavelength band can extend from about 10 nm to about 400 nm, the included UV wavelength ranges can be collectively referred to herein as mid-wavelength.

According to an exemplary embodiment of the present disclosure, a differential sterilization ultraviolet sleeve can be provided that can include a longitudinal flexible structure at least about 1 centimeter long, a longitudinal lumen and an optical component. The longitudinal lumen can be open at a proximal end and open at a distal end inside the flexible structure, and can be configured to pass a percutaneous structure. The optical component can be disposed outside the lumen and can be configured to diffuse ultraviolet light only in a wavelength range from about 190 nanometers to about 230 nanometers. The optical component can include an optical coupler configured to be coupled in optical communication with an optical source.

In some embodiments of the present disclosure, the sleeve can be configured as a Chinese finger trap comprising a weave of several strands, and the optical component can include an optical fiber(s) disposed as a strand(s) of the weave. The optical component can include multiple diffusing rings, each ring can be connected by a corresponding separate optical fiber to the optical coupler. In some exemplary embodiments of the present disclosure, a system can include the differential sterilization ultraviolet sleeve and an optical source configured to provide, to the optical coupler, ultraviolet light in the wavelength range from about 190 nanometers to about 230 nanometers at a power level of at least about 0.04 milliWatts per centimeter squared of an area of an outer surface of the sleeve.

A further exemplary embodiment of the present disclosure can comprise a method that includes inserting a percutaneous structure through a lumen of a differential sterilization ultraviolet sleeve. The sleeve can include an optical component configured to diffuse ultraviolet light only in a wavelength range from about 190 nanometers to about 230 nanometers. The method can also include implanting the percutaneous structure in a subject such that the sleeve can be disposed below a skin level of the subject from the skin level for a distance of at least about 1 centimeter. The exemplary method can further include coupling the sleeve to be in optical communication with an optical source configured to provide ultraviolet light in the wavelength range from about 190 nanometers to about 230 nanometers at a power level of at least about 0.04 milliWatts per centimeter squared of an area of an outer surface of the sleeve. The method can also include operating the source to provide the light to the sleeve according to a temporal schedule.

In some exemplary embodiments of the present disclosure, the temporal schedule can be continuous for a duration of the percutaneous structure being implanted in the subject.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Embodiments are illustrated by way of example, and not by way of limitation, in the figures of the accompanying drawings in which like reference numerals refer to similar elements and in which:

FIG. 3 is a diagram that illustrates exemplary separate contouring sleeve system when implanted around a percutaneous structure according to an exemplary embodiment of the present disclosure;

Figure 1:
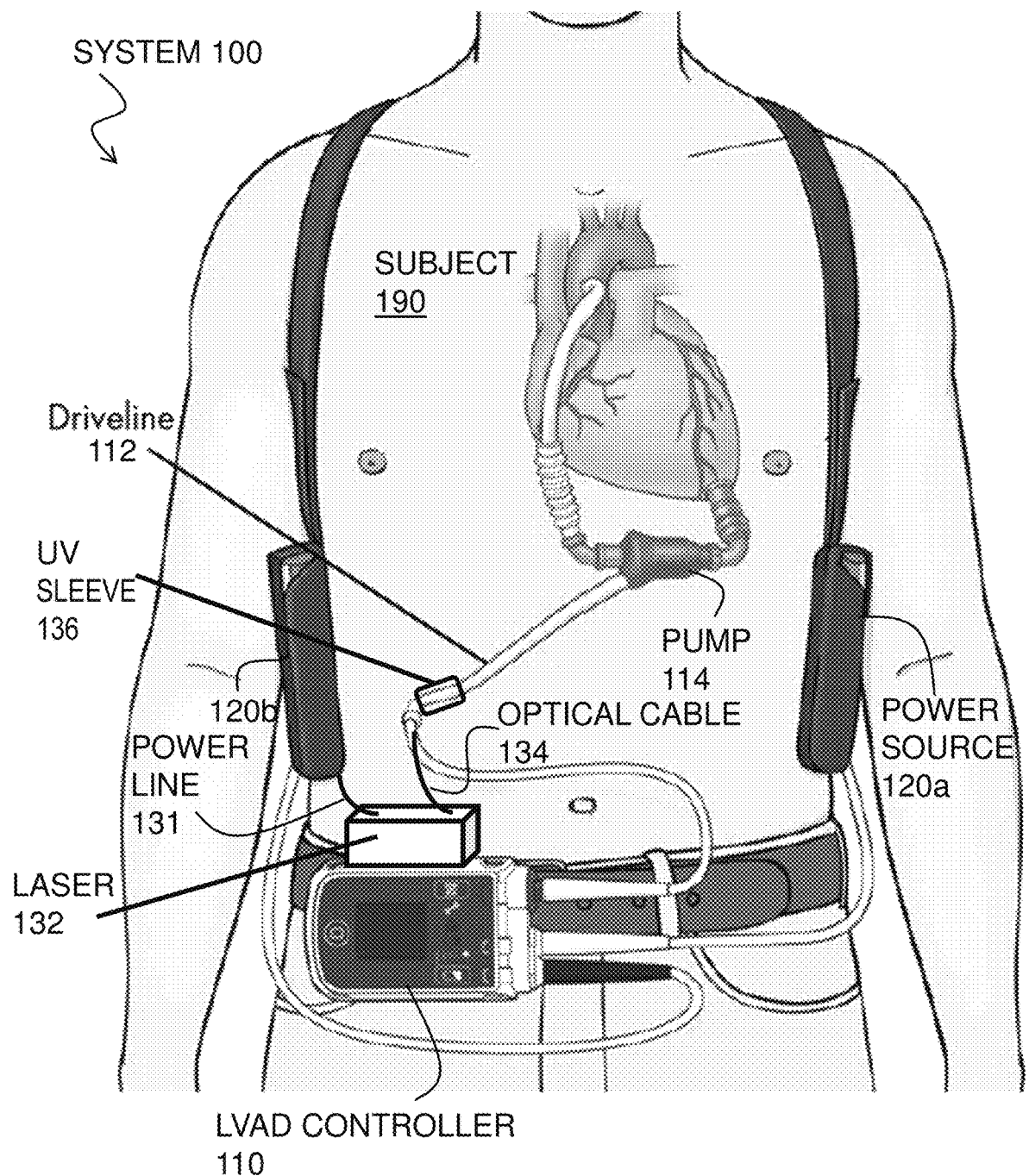
FIG. 1 is a diagram that illustrates an exemplary ultraviolet sleeve for preventing or retarding adventitious infection related to left ventricular assist device implantation according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

A method, system and apparatus according to an exemplary embodiment of the present disclosure are described for prevention or retardation of adventitious infection on percutaneous structures using mid-wavelength ultraviolet radiation. In the following description, for the purposes of explanation, numerous specific details can be set forth in order to provide a thorough understanding of the present disclosure. It will be apparent, however, to one skilled in the art that the present disclosure can be practiced without these specific details. In other instances, well-known structures and devices are shown in diagram form in order to avoid unnecessarily obscuring the present disclosure.

Some exemplary embodiments of the present disclosure are described below in the context of LVAD with a removable contouring UV sleeve, although not limited thereto. In other exemplary embodiments of the present disclosure, the percutaneous device or structure can be or include one or more of a LVAD Driveline, LVAD Pump, Arteriovenous ECMO Cannula, Colostomy Apparatus, Foley Catheter, Tracheostomy Cannula, Thoracostomy Tube, Intravenous Line, Central Venous Pressure Line, Cordis Introducer, Arterial Line, Pulmonary Artery Monitoring Catheter (e.g., Swan-Ganz), Veno-Venous ECMO line, Peritoneal Dialysis Catheter, Hemodialysis Catheter, PICC line (e.g., Peripherally Inserted Central Catheter), T-Tube (e.g., or Bile Drainage after Common Duct Exploration), Pacemaker Generator, Implantable Defibrillator Generator ("ICD"), Venous Access Port (e.g., Chemotherapy), Vascular Graft for Aorta or Large Arteries and Veins, Total Artificial Heart, New Generation LVAD pump. Additionally, the UV sleeve can be permanently attached to the percutaneous device or structure, the optical components of the sleeve can be integrally part of such percutaneous structures or some combination thereof.

Thus, various exemplary embodiments of the present disclosure relate to the protection of percutaneous structures (e.g., a prosthetic material) implanted in the human body from the adventitious infection. Such infection can be initiated by glycoprotein deposition, which can facilitate a bacterial adherence into a slime layer. A biofilm can then form, promoting bacterial growth and antibiotic resistance. For tubes, catheters and cannulas, similar processes can occur, both on external surfaces exposed to the subcutaneous space/mucous membranes or to the internal surface, which can communicate with the blood stream, urinary bladder, digestive system or other contiguous spaces. Bacteria can usually enter at the prosthetic-cutaneous interface, and septic processes or breaks in the technique can also contaminate the implanted devices from within.

UV radiation in the range of about 200-225 nanometer wavelength range can beneficially impact current approaches to sterilization of percutaneous devices. A Kr—Br excimer lamp has been shown to effectively kill methicillin resistant staphylococcal aureus in vitro, with minimal injury to human skin fibroblasts. (See, e.g., Reference 1). Additionally, a UV source confined to the mid-wavelength range of about 190 nm to about 230 nm can be suitable for killing bacteria without harm to human tissue. (See, e.g., Reference 2). The exemplary results can be applied to the clinical arena for a continuous or intermittent differential UV irradiation sterilization ("DUVS") system that can sterilize a prosthetic surface without injury to surrounding human tissues (e.g., "differential sterilization" can be used to indicate sterilization by killing bacteria, fungi or viruses without injuring human cells). Thus, as described herein, the process of contamination can be prevented by continuous or intermittent DUVS radiating UV light of a specific wavelength chosen among those in the range from about 190 to about 230 nm. DUVS can be cytotoxic to bacteria, fungi and viruses, but not harm human cells in vitro.

In various exemplary embodiments of the present disclosure, methods and systems can be provided for optical conduction of UV light within a mid-wavelength band for sterilization of percutaneous structures, such as LVAD drivelines. For example, a lightweight, battery powered laser operating at a UV wavelength of about 220 nm, or otherwise in a mid-wavelength band, can be connected through an optical cable and optical coupler to flexible light guides, such as optical fibers, configured to balance transmission and radiation, such that mid-wavelength UV energy introduced into the fiber can dissipate over the length of the fiber. The leaked energy can radiate into the surrounding tissues. In some exemplary embodiments of the present disclosure, the optical light guides can be woven in a sleeve that can either be fixed or otherwise connected to the percutaneous structure, or configured to be stretched to removably fit the contours of one or more different percutaneous structures, such as various LVAD drivelines.

According to some exemplary embodiments of the present disclosure, generation and radiation of DUVS from the implant itself can be provided, for example, employing electroluminescence and external power. In some exemplary embodiments of the present disclosure, UV radiation can be generated externally and conducted to an implant constructed of material that can conduct UV light and can leak it to internal and external surroundings. Some embodiments can include equipping the implant with a radiator (e.g., a sleeve or attachment) that radiates UV light. In various exemplary embodiments of the present disclosure, the source of the UV light can be an electroluminescence or a built-in laser, and/or it can be externally generated by a laser or other source and conducted to the radiator by fiber optics. In some exemplary embodiments of the present disclosure, laser energy can be transmitted parallel to the electrical system of a hospital by fiber optic networks connected to a powerful, centrally located UV radiation laser system and connected to the DUVS device.

Figure 6A:
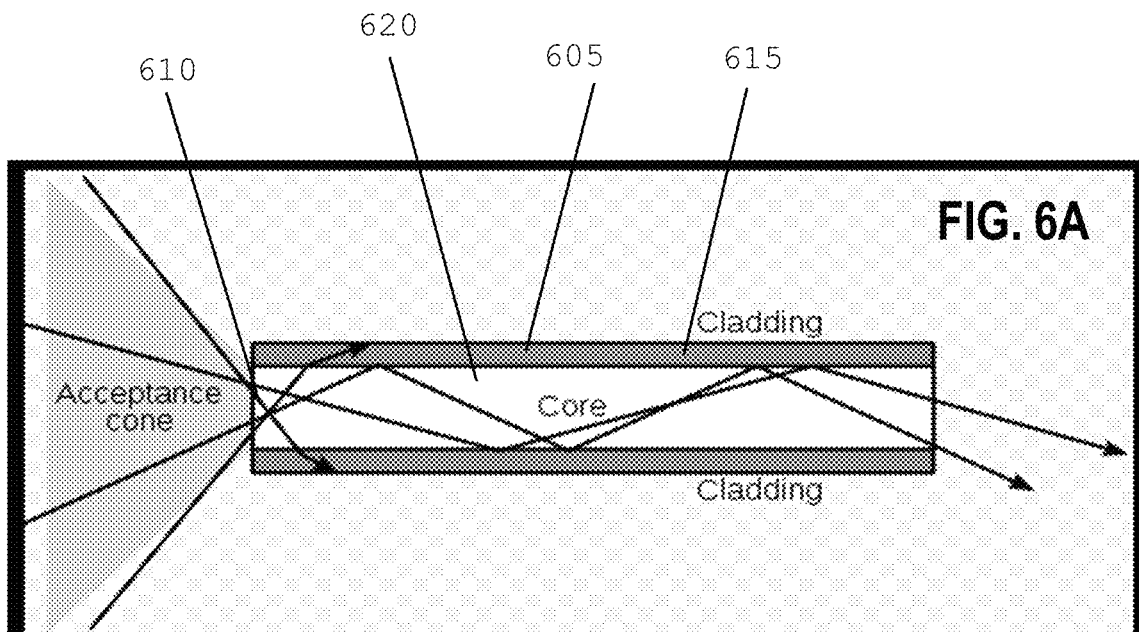
FIG. 6A is a diagram that illustrates exemplary coupling of light into an optical fiber according to an exemplary embodiment of the present disclosure.

Applications in telecommunications and information technology can utilize sophisticated multilayered optical fibers. Light can be conducted by, for example, a quartz or silica glass core. The core can be surrounded by cladding. The refractive index of the junction between the cladding and the core can be optimized to reflect and redirect light attempting to escape from the core. FIG. 6A shows a diagram that illustrates an exemplary coupling or providing of light radiation into an optical fiber 605, according to an exemplary embodiment of the present disclosure. The optical fiber 605 can accept and propagate the light incident on a proximal end of the optical fiber 605 in an acceptance cone 610. Steeper rays of incident UV light can be lost in the cladding 615, and may not propagate along the core 620 of the optical fiber 605. A buffer layer 640 and external jacket 635 (see FIG. 6B) can be added for protection and increased durability in some exemplary embodiments.

Figure 6B:
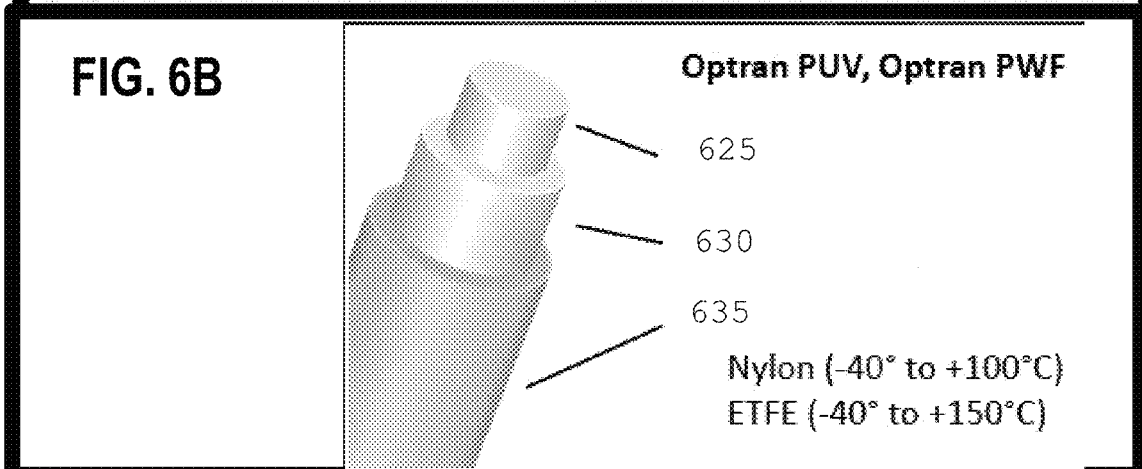
FIGS. 6B and 6C are diagrams that illustrate exemplary optical fibers for use in a sleeve according to an exemplary embodiment of the present disclosure.
Figure 6C:
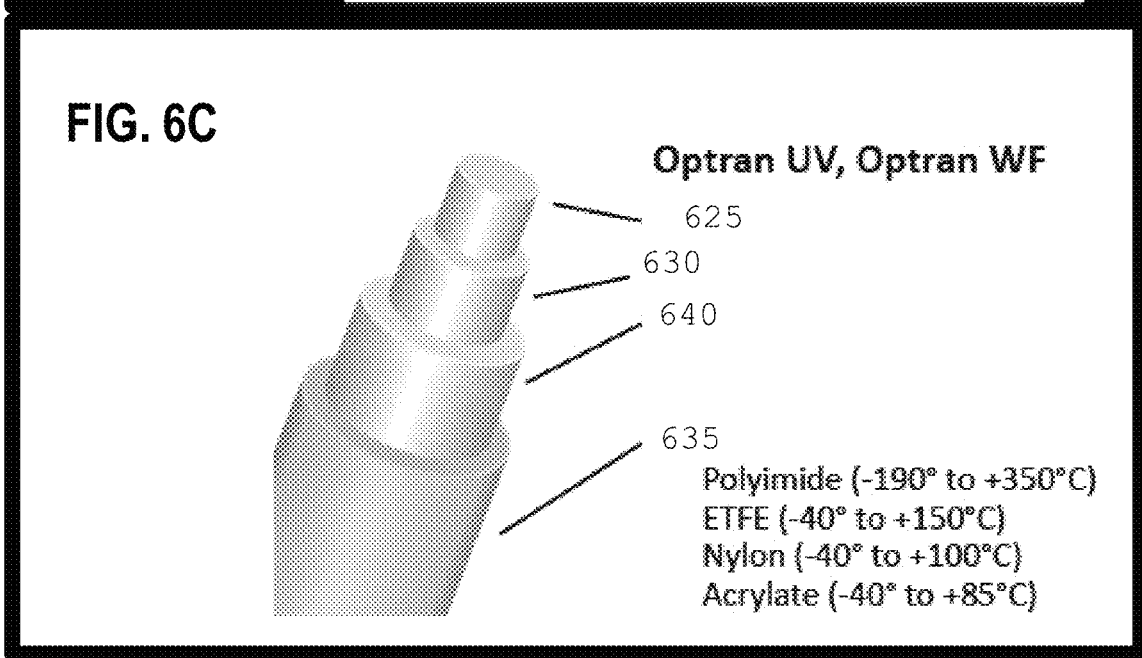

FIG. 6B and FIG. 6C shows diagrams that illustrate exemplary optical fibers for the use in a sleeve or other DUVS device, according to an exemplary embodiment of the present disclosure. These exemplary layers can be integrated with a high degree of quality control by the manufacturer. The utility of optical fibers can be affected by the diameter and the composition of the component layers. Core materials can include a silica core 625 (e.g., pure/fused or germanium doped) and mixed silver halide. Claddings 630 include silicone, fluorine doped silicone, hard polymer and mixed silver halide. Pure silica tubing can be available. For UV radiation applications, for example, Polytetrafluoroethylene cladding can be useful. Suitable bend radii can be about 50-150 times the clad diameter. Representative core diameters can be about 25-2,000 microns (e.g., also called micrometers, mm, 1 mm=$10^{-6}$ meters).

Certain advantageous properties of a DUVS device formed from optical fibers can include: (i) durability (e.g., to support continuous function for up to about five years), (ii) redundancy (e.g., so that if one fiber breaks, there can be a another fiber to provide continued illumination and sterilization), (iii) flexibility (e.g., so DUVS does not interfere with normal flexion of drive line or other percutaneous structure), (iv) radius of curvature without breakage (e.g., so fiber can conform to radius of drive line or other percutaneous structure without fracture), (v) UV light transmission (e.g., adequate UV fluence at distal end to provide sterilization function), (vi) UV light Leakage (e.g., to provide illumination levels that can be cytotoxic along length of device), and (vii) low manufacturing complexity (e.g., to keep costs at or below about $2,000). Various design characteristics can be employed, including symmetrical or asymmetrical shape, homogenous or heterogeneous longitudinal fiber properties, and simple or complex geometry.

FIG. 1 shows an exemplary diagram that illustrates an exemplary system which includes an exemplary UV sleeve for preventing or retarding adventitious infection related to LVAD implantation, according to an exemplary embodiment of the present disclosure. The exemplary LVAD system 100 can include a LVAD controller 110, a driveline 112 and a pump 114, and can be powered by one or more powers sources 120a, 120b, such as, for example, batteries. The driveline 112 can include an external and internal portion. The internal portion can be or include a percutaneous structure subject to adventitious infection. According to the exemplary embodiment of the present disclosure, a UV sleeve 136, which is configured to emit mid-wavelength UV light absent longer and shorter UV RADIATION wavelengths, can surround a portion of the percutaneous structure. The exemplary UV sleeve can receive a mid-wavelength UV radiation beam along optical cable 134 from a mid-wavelength UV radiation source (e.g., a laser 132), which can be powered by the power source 120b through a power line 131. In some exemplary embodiments of the present disclosure, the sterilization components can be collectively termed a DUVS system and can be attached to subject 190.

Figure 2A:
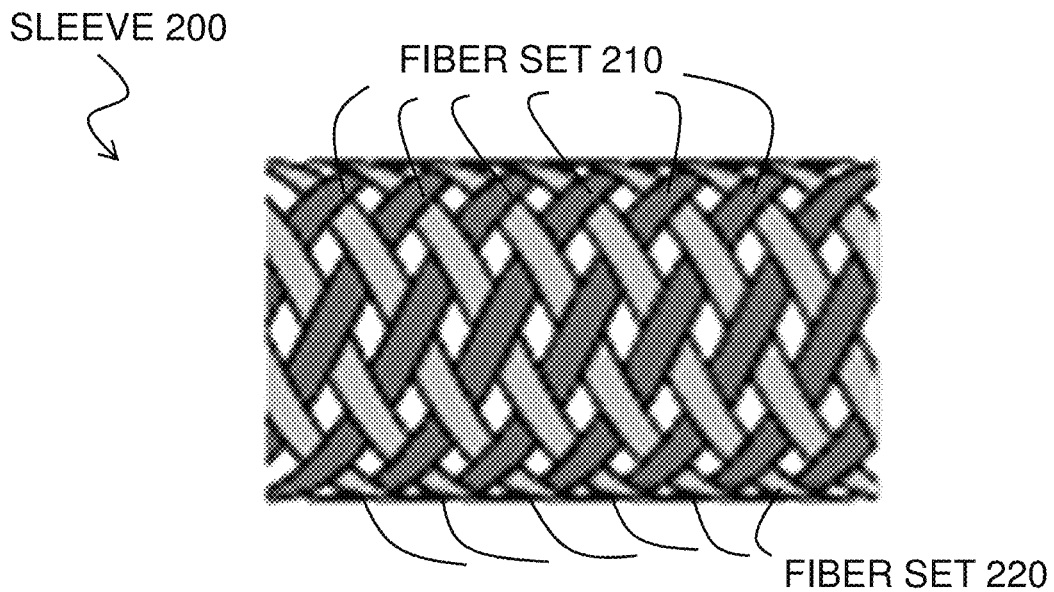
FIG. 2A is a diagram that illustrates an exemplary separate contouring sleeve comprising ultraviolet (UV) light emitting optical fibers according to an exemplary embodiment of the present disclosure.

FIG. 2A shows an exemplary diagram that illustrates an exemplary separate contouring sleeve 200 including UV light emitting optical fibers, according to an exemplary embodiment of the present disclosure. The exemplary sleeve 200 can include a first fiber set 210 of parallel counterclockwise spiral fibers enclosing a roughly cylindrical lumen interwoven with a second fiber set 220 of parallel clockwise spiral fibers enclosing the same lumen. The enclosed roughly cylindrical lumen can have a length in an axial direction and a width, or diameter, in a radial direction. At least one fiber of the first fiber set 210 or of the second fiber set 220, can be or include an optical fiber configured to transmit and/or emit the UV radiation in a mid-wavelength range. In some exemplary embodiments of the present disclosure, most or all of the fibers in either the first fiber set 210 or all or most of the fibers in the second fiber set 220, or some combination of fibers in the first fiber set 210 and the second fiber set 220, can be optical fibers configured to transmit and emit UV radiation in a mid-wavelength range.

Such exemplary configuration can be based on the Chinese finger trap, or Kellens cable puller. The exemplary configuration can be or provide a biaxial braid, symmetrical positioned around the long axis. Component fibers can be longitudinally homogeneous, but, as described below, optical properties of the fibers can be heterogeneous along the fiber in some exemplary embodiments. The underlying geometry can be complex and can be characterized by the diameter and the length of the sleeve, and the angle between the braids at their crossing points. Pulling the ends of the sleeve can increase the length, decrease the diameter and decrease the angle of the crossings relative to the long axis of the sleeve. The exemplary sleeve may not have to precisely fit the driveline or other percutaneous structure, since the sleeve can be shortened and widened to fit over the end of the percutaneous structure and then can be stretched and narrowed for precise fit.

Optimizing the exemplary finger trap sleeve embodiment can include a tradeoff of UV conduction/leakage vs. handling properties. It can be advantageous in the finger trap design to balance linear transmission/leakage properties such that bactericidal or bacteriostatic UV energy can leak along the length of the fiber. This exemplary design can utilize a quartz (e.g., silica glass) core and TeflonAF cladding. Representative commercial Teflon AF 2400 tubing can include thin walled and thick walled variants. The commercially-available thin walled Teflon AF 2400 tubing can include the following cladding outer diameter ("OD") and inner diameter ("ID") specifications in inches given in Table 1, where the glass core diameter can match the cladding inner diameter.

TABLE 1

Exemplary commercially available optical fibers.

| Thin wall OD | Thin wall ID | Thick wall OD | Thick wall ID |
|---|---|---|---|
| 0.040" | 0.032" | 0.074" | 0.061" |
| 0.032" | 0.024" | 0.063" | 0.0394" |
| 0.029" | 0.024" | 0.035" | 0.0139" |
| 0.016" | 0.009" | 0.035" | 0.0096" |
| 0.012" | 0.009" | 0.032" | 0.014" |
| 0.010" | 0.008" | 0.020" | 0.003" |

Exemplary optical fibers suitable for one or more fibers in the fiber set 210 or fiber set 220 can include Optran UV/WF, from Ceramoptec™ of Bonn, Germany, which can transmit about 90% of carried light per meter, indicating a diffusion of about 10% per meter, for the UV wavelengths between about 200 and about 220 nm.

Exemplary configurations for either or both fiber sets 210 and 220 can include tight packed spirals and gapped spirals. Optran fibers have core diameters from about 200 to about 2000 microns core diameter, and cladding can add about 10-20% thickness. About 1,000 windings of the smallest fiber tightly packed can cover a driveline length of about 20 cm, and about 100 windings of the larger fiber can be sufficient. Fiber length can be about 300-3,000 centimeters. This can be the upper limit of the fiber length used by the exemplary device. More acute angles can produce gaps between fiber windings.

In exemplary embodiments of the present disclosure in which at least some fibers may not be optical fibers, the fibers can be selected to provide structural integrity, or support or flexibility or elasticity to the sleeve, or some combination thereof. Examples of such non-optical fibers can include fibers made of cloth, epoxy, metal, elastic, plastic, Teflon and nylon, either alone or in some combination.

In some exemplary embodiments of the present disclosure, the sleeve can further be configured to be stretched or contracted in the axial direction from a rest state. As the sleeve can be stretched in the axial direction, the width can decrease in the radial direction. Conversely, as the sleeve can be contracted in the axial direction, the width can increase in the radial direction. The length of the lumen inside the sleeve 200 in the rest state can be called the rest length, and the corresponding diameter of the lumen inside the sleeve 200 in the rest state can be called the rest diameter. This capacity to be stretched or contracted in the length or corresponding diameter can be indicated herein by the term "contouring" when used with the sleeve. The percutaneous structure being contoured by the sleeve 200 need not be cylindrical, with a circular or oval cross section, but can include structures with regular or irregular polygonal cross sections. Additionally, the percutaneous structure does not need to be of uniform diameter, but the sleeve can snugly fit the structure even with some variation in diameter of the structure along the axial direction of the sleeve. The exemplary spiral configuration of each optical fiber can facilitate the contraction or stretching of the contouring sleeve without breakage of the optical fiber. Exemplary ranges of contraction and expansion in various embodiments include 0 to 100%. For example, lengths of a cylindrical finger trap of constant diameter can be about 10, 12, 14, 16, 18 and 20 cm corresponding to increases of about 0%, 20%, 40%, 60%, 80% and 100% compared to a baseline length of about 10 cm. The resulting decreases in diameter based on constant surface area can be 0%, 9%, 16%, 21%, 25% and 29%, respectively.

In some exemplary embodiments of the present disclosure, the contouring sleeve can be used with a percutaneous structure of one or more devices by passing the percutaneous structure through the lumen of the sleeve in a state of contracted or rest length, and then releasing or stretching the sleeve until the sleeve fits snugly over the percutaneous structure. For example, according to some exemplary embodiments of the present disclosure, a contouring sleeve can be used with a portion of driveline 112 by passing the driveline through the lumen of the sleeve 200, then stretching the sleeve 200 until it fits snugly over the driveline. In some exemplary embodiments of the present disclosure, the sleeve can be maintained in a stretched, snug configuration by anchoring a distal end of the sleeve to the percutaneous structure. According to other exemplary embodiments of the present disclosure, the driveline o can pass through the lumen of the sleeve 200 when the sleeve is in a contracted length state, then the sleeve 200 can be released until the sleeve fits snugly over the driveline. In such exemplary embodiments, the sleeve may likely not be maintained in a stretched configuration, and anchoring to the percutaneous structure may not be performed at the distal end of the sleeve.

Figure 2B:
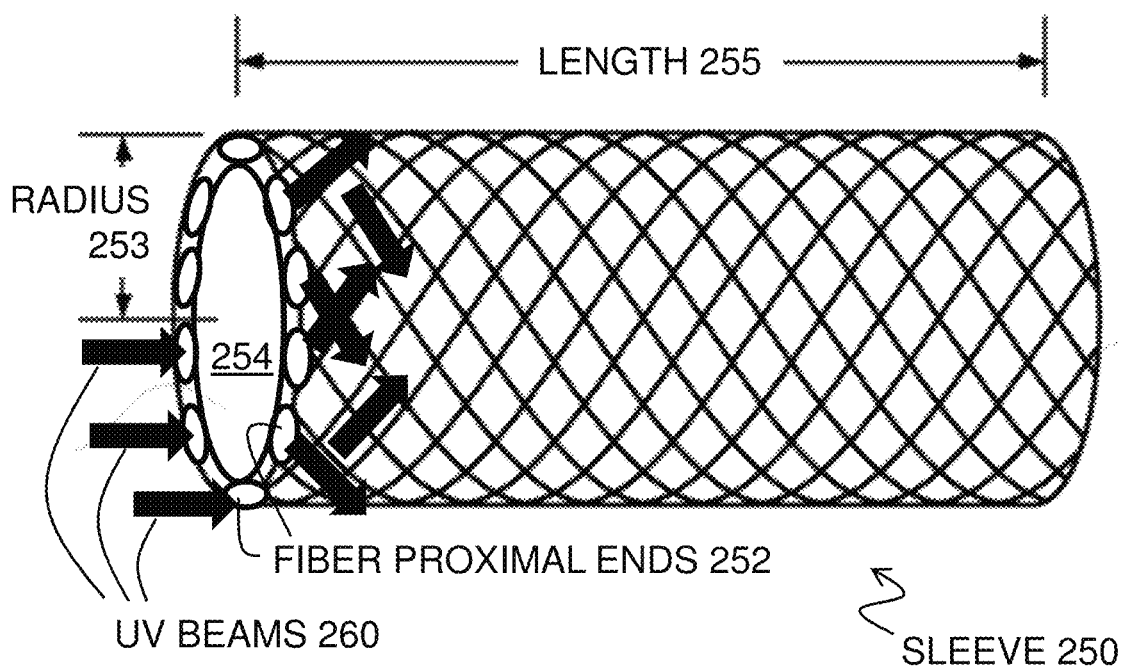
FIG. 2B is a diagram that illustrates exemplary coupling and propagation of UV radiation in a contouring sleeve according to an exemplary embodiment of the present disclosure.

FIG. 2B shows an exemplary diagram that illustrates exemplary coupling and propagation of UV radiation in a contouring sleeve 250, according to an exemplary embodiment of the present disclosure. In this exemplary embodiment, it can be assumed for purposes of illustration, that every fiber in both counterclockwise spiraling fiber set 210 and clockwise spiraling fiber set 220 can be an optical fiber. The proximal ends 252 of, for example, ten optical fibers are depicted in FIG. 2B, including proximal ends 252 of five optical fibers in the counterclockwise spiraling fiber set 210 and proximal ends 252 of five more optical fibers in the clockwise spiraling fiber set 220. Together, the two optical fiber sets construct a sleeve 250 of rest length 255, and rest outer radius 253 (e.g., with lumen radius less than the outer radius 253 by an average diameter of the optical fibers).

Lumen lengths and lumen diameters can depend on dimensions of percutaneous structures. Furthermore, in some exemplary embodiments of the present disclosure, a textured outer surface of the sleeve 200 or the sleeve 250 can be desirable, such as when some adherence to the skin of the subject can be desirable. In some exemplary embodiments of the present disclosure, a smooth outer surface can be advantageous, such as when adherence to connective tissue may not be desired. For example, a textured sleeve with a lumen diameter of about 10 millimeters (e.g., mm, 1 mm=10-3 meters), give or take a factor of two, and greater, can be desirable for a LVAD driveline, LVAD pump, an arteriovenous extracorporeal membrane oxygenation ("ECMO") cannula, and a colostomy apparatus. In other exemplary embodiments of the present disclosure, a smooth sleeve with a lumen diameter of about 10 mm and greater can be provided for a Foley catheter, a tracheostomy cannula and a thoracostomy tube. In yet other exemplary embodiments of the present disclosure, a smooth sleeve with a lumen diameter of about 1 to about 3 mm, give or take a factor of two, can be desirable for several percutaneous structures that can be in place a short time (e.g., on the order of days), including an intravenous line, central venous pressure line, cordis introducer, arterial line, pulmonary artery monitoring catheters such as Swan-Ganz catheters, veno-venous ECMO line, peritoneal dialysis catheter, hemodialysis catheter, peripherally inserted central catheter ("PICC") line for chemotherapy, and a T-tube for bile drainage after common duct exploration. Specific exemplary dimensions tailored for certain devices and permanent integration of the sleeve, rather than a removable configuration, can be appropriate in some exemplary embodiments, including for a pacemaker generator, an implantable cardiac defibrillator ("ICD") generator, a venous access port for chemotherapy, a vascular graft for aorta or other large arteries or for veins, a total artificial heart, and a further exemplary LVAD pump.

As shown in FIG. 2B, UV beams 260 of UV light can be in a mid-wavelength band directed into the proximal ends 252, and propagating along each optical fiber in the sleeve 250. An optical coupler can cause the UV beams 260 to enter the proximal ends of each optical fiber. As the beams 260 propagate along the optical fibers, the UV radiation in the UV mid-wavelength range can be emitted into the surrounding tissue, killing bacteria that can be present but leaving the tissue relatively unharmed. Thus, the UV light in the mid-wavelength range that can propagate along the sleeve 250 can differentially sterilize the tissue adjacent to the sleeve 250. For example, at least about 0.15 joules per square centimeter ($J/cm^2$) for the life cycle of a bacterium (minutes to hours) can be sufficient for this purpose.

This amounts to a power level of about 2 milliWatts (e.g., mW, 1 mW=10-3 watts, 1 watt=1 joule per second) per square centimeter of the sleeve surface area if applied over a short time (e.g., two minutes) to a smaller power level of about 0.04 $mW/cm^2$ of the sleeve surface area if applied over the longer time (e.g., one hour). For a sleeve about 10 cm long with a diameter of about 1 cm, the surface area can be about 32 $cm^2$ and the power requirement can be as high as about 60 mW down to about 1 mW. Any level in this range can be applied continuously. In other exemplary embodiments of the present disclosure, the same or higher power level can be applied intermittently, for example, twice the power can be applied for one or more hours and turned off for one or more hours. In some exemplary embodiments of the present disclosure, the power level can be applied continuously for the first 24 hours and the same or different power level can be applied intermittently thereafter.

FIG. 3 shows an exemplary diagram that illustrates an exemplary separate contouring sleeve system 300 when implanted around a percutaneous structure, according to an exemplary embodiment of the present disclosure. The exemplary sleeve system can include sleeve 301, such as the sleeve 200 or the sleeve 250. The system 300 can also include an optical coupler 320, a mid-wavelength UV source 324, a sleeve UV controller 340, a proximal anchor 310 and a distal anchor 312. Also shown is the skin level 390 of a subject and a percutaneous structure 380 for purposes of illustration.

The mid-wavelength UV source can be configured to provide UV radiation at one or more wavelengths in the UV mid-wavelength range, and can exclude UV radiation outside the UV mid-wavelength range. For example, in various exemplary embodiments of the present disclosure, the UV source can be a laser or a light emitting diode ("LED") or some combination thereof. For example, an experimental laser operating at a wavelength less than about 224 nm is available.

In some exemplary embodiments of the present disclosure, the UV source 324 can include one or more filters that can block UV radiation outside the UV mid-wavelength range. For example, a custom bandpass filter removed all but dominant 207-nm wavelength emission.

The optical cable 322 can include one or more optical fibers that carry the UV radiation provided by the source 324. For example, in some embodiments a CWA-SMA-200-U-2 Fiber Optic Patch Cord with SMA 905 connector and 200 micrometer core—UV/VIS-2 m can be used. In some exemplary embodiments of the present disclosure, the optical cable can include one or more filters that can block UV radiation outside the UV mid-wavelength range.

The optical coupler 320 can be configured to direct light received via the optical cable 322 into the proximal ends 252 of one or more optical fibers in the sleeve 301. The optical coupler 320 can also be shaped to facilitate a percutaneous structure 380 to pass through the coupler 320. As described herein, for example, an optical couple can be any device or configuration that can facilitate or control the propagation of light in one or more wavelengths or wavelength bands selected from infrared wavelengths through visible wavelengths and into UV wavelengths, inclusively. Optical couplers can include one or more of free spaces, vacuum chambers, gas-filled chambers, optical fibers, mirrors, beam splitters, lenses, crystals, glasses, or other shaped or layered materials, Y shaped splitters, or fan shaped fiber bundles, alone or in some combination. In some exemplary embodiments of the present disclosure, the optical coupler 320 can include one or more filters that can block UV radiation outside the UV mid-wavelength range. In one exemplary embodiment, the coupler can be a low grade fiber splitter.

The exemplary sleeve can be fixed to a proximal anchor that can be configured to be attached to a skin level 390 of a subject. In some exemplary embodiments of the present disclosure, the anchor can include a flange or wing configured to be glued or stitched or taped to the skin, such as with bandage tape. For example, in one exemplary embodiment of the present disclosure, the sleeve can be anchored to the drive line with 2-0 polypropylene tape. Between the optical coupler and the proximal anchor 310 can be an external portion 303 of sleeve 301 and system 300. Between the proximal anchor 310 and a distal end of the sleeve 301 can be an internal portion 305 of the sleeve 310 and system 300.

In some exemplary embodiments of the present disclosure, the distal end of the sleeve includes a distal anchor 312 configured to be attached to the percutaneous structure 380, for example, with fasteners, or glue, or tape. The distal anchor 312 can be advantageous in exemplary embodiments in which the percutaneous structure 380 has a diameter along all or part of the length of the structure 380, which diameter can be less than a rest lumen diameter of the sleeve 301. In some such exemplary embodiments of the present disclosure, the sleeve 301, or at least the internal portion 305 of the sleeve 301, can be stretched to an internal distance 314 at which length the lumen diameter contracts sufficiently to snugly fit the percutaneous structure 380. The distal end of the sleeve 301 can be anchored to the percutaneous structure at distance 314 to prevent or inhibit the sleeve 301 from returning to the rest length, and thus the rest diameter apart from the percutaneous structure 380, while both can be implanted in a subject.

The sleeve UV controller 340 can be configured to operate the mid-wavelength UV source to provide a therapeutically effective amount of mid-wavelength UV illumination along the distance 314 of the internal portion 305 of the sleeve 301. In some exemplary embodiments of the present disclosure, the mid-wavelength UV source can be operated continuously, and a separate controller can be omitted. In some exemplary embodiments of the present disclosure, however, it can be advantageous to operate the mid-wavelength UV source 324 intermittently, for example, at high intensity for a few hours followed by a hiatus for several minutes or hours. A therapeutically effective illumination of the sleeve 301 by the mid-wavelength UV source 324 can vary with the percutaneous structure, the dimensions and materials of the sleeve 301, and the individual subject. Thus, the controller 324 facilitates the exemplary system 300 to be usable for a particular use. In some exemplary embodiments of the present disclosure, the controller 324 can be programmable and can be implemented, in various embodiments, as software or hardware in a general purpose computer system as described below with reference to FIG. 8 or in a hardware configuration as described below with reference to FIG. 9, or some combination thereof. For example, the sleeve can be illuminated continuously for the first 24 hours and intermittently (e.g., on for one minute and off one to five minutes) thereafter.

Figure 4A:
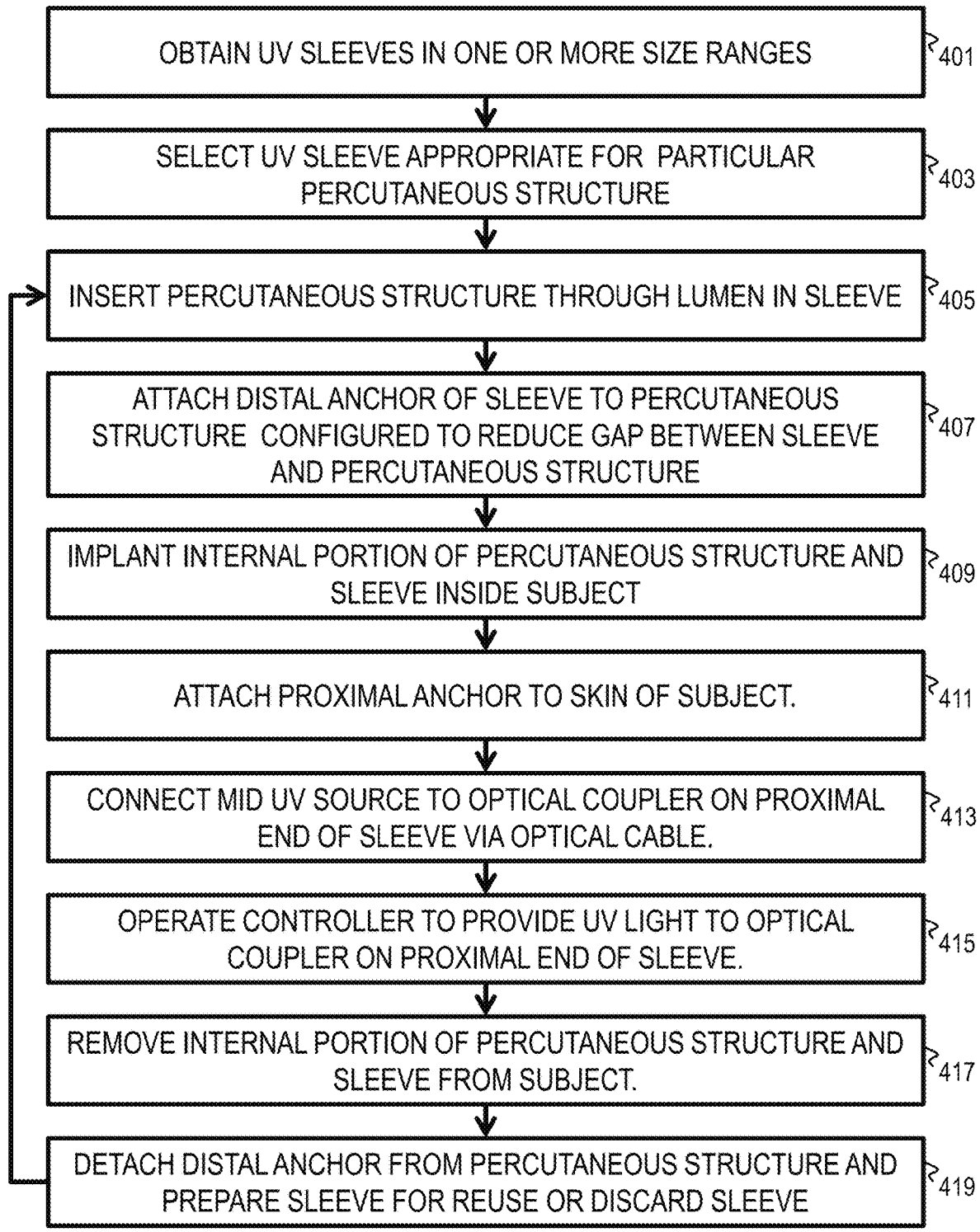
FIG. 4A is a flow chart that illustrates an exemplary method for using contouring sleeve system to prevent or retard adventitious infection according to an exemplary embodiment of the present disclosure.

FIG. 4A shows an exemplary flow chart that illustrates an exemplary method 400 for use of a separate contouring sleeve system to prevent or retard adventitious infection, according to an exemplary embodiment of the present disclosure. Although procedures are depicted in the flow chart of FIG. 4A as integral procedures in a particular order for purposes of illustration, in other embodiments, one or more procedures, or portions thereof, can be performed in a different order, or overlapping in time, in series or in parallel, or can be omitted, or one or more additional procedures can be added, or the method can be changed in some combination of ways.

As illustrated in FIG. 4A, at procedure 401, a separate UV sleeve can be obtained in each of one or more size ranges, for example, by manufacture or purchase. For example, contouring UV sleeves can be manufactured using any method, or can be obtained from a manufacturer. For example, one or more optical fibers can be braided with zero or more fabric strands to form a Chinese finger trap weave pattern. The free ends of the weave can become the proximal end for connecting to the optical coupler. Size ranges with resting lumen diameters can vary from about 1 mm to greater than about 10 mm (e.g., give or take a factor of two) and lengths from about 1 centimeter (e.g., cm, 1 cm=10-2 meters) to about 10 cm (e.g., give or take a factor of two) can be produced or obtained in various exemplary embodiments.

At procedure 403, a separate UV sleeve can be selected for a particular purpose. For example, a textured surface, contouring sleeve with a resting lumen diameter of about 11 mm can be selected for a LVAD driveline 112.

At procedure 405, the percutaneous structure can be inserted through the lumen in the sleeve. For example, the LVAD driveline 112 can be inserted as percutaneous device 380 through the lumen in sleeve 301, and through or past optical coupler 320, and through or past distal anchor 312. In procedure 407, the distal anchor 312 can be attached or otherwise affixed to the percutaneous structure at a distance such that the sleeve can be stretched, and any gap between the percutaneous device and the sleeve can be reduced or eliminated. For example, the textured surface, contouring sleeve with a resting lumen diameter of about 11 mm can be stretched from about 5 cm to about 6 cm, and can be affixed by a distal anchor to a driveline 112.

As a result of the stretching, the lumen diameter can be contracted from about 11 mm to about 10 mm; and, as a result, the sleeve 301 can fit snugly against the drive line 112. In some exemplary embodiments of the present disclosure, the resting lumen diameter can be equal to, or less, than the diameter of the percutaneous structure along all or most of the length of the sleeve, and therefore, a distal anchor 312 may not be used, and thus, procedure 407 can be omitted. In some exemplary embodiments of the present disclosure, a percutaneous device can be obtained with a sleeve already affixed or otherwise attached, and procedures 401 through 407 can be omitted.

At procedure 409, the internal portion of the percutaneous structure and sleeve can be implanted inside a subject using any standard procedures. At procedure 411, the proximal anchor 310 of the sleeve can be attached to a skin of the subject at a skin level 390.

At procedure 413, a mid-wavelength UV source, such as the source 324, can be connected via optical cable, such as the cable 322, to an optical coupler, such as the optical coupler 320, on a proximal end of the sleeve 301, such as the sleeve 301. At procedure 415, the UV sleeve controller, for example, the controller 324, can be operated to control the UV source to produce a continuous, or one or more pulses of a UV beam including one or more wavelengths in the mid-wavelength UV range to cause a therapeutically effective amount of mid-wavelength UV radiation to be delivered into the tissue of the subject along all or most of the length of the internal portion of the sleeve, such as the internal portion 305 of the sleeve 301.

At procedure 417, upon completion of the use of the percutaneous structure, the internal portion of the percutaneous structure and UV sleeve can be removed from inside the subject. At procedure 419, the percutaneous structure can be removed from within the lumen of the UV sleeve. In some exemplary embodiments of the present disclosure, this can include detaching the distal anchor from the percutaneous structure. If the UV sleeve or percutaneous device can be re-usable, the re-usable item can be prepared for re-use, for example, by washing or disinfecting. If a separate UV sleeve can be re-used, control can pass back to procedure 405, to pass another percutaneous structure through the lumen of the UV sleeve prepared for reuse. In some exemplary embodiments of the present disclosure, the UV sleeve may not be removable, and procedure 419 comprises simply discarding or re-using the percutaneous structure and UV sleeve combination.

Figure 4B:
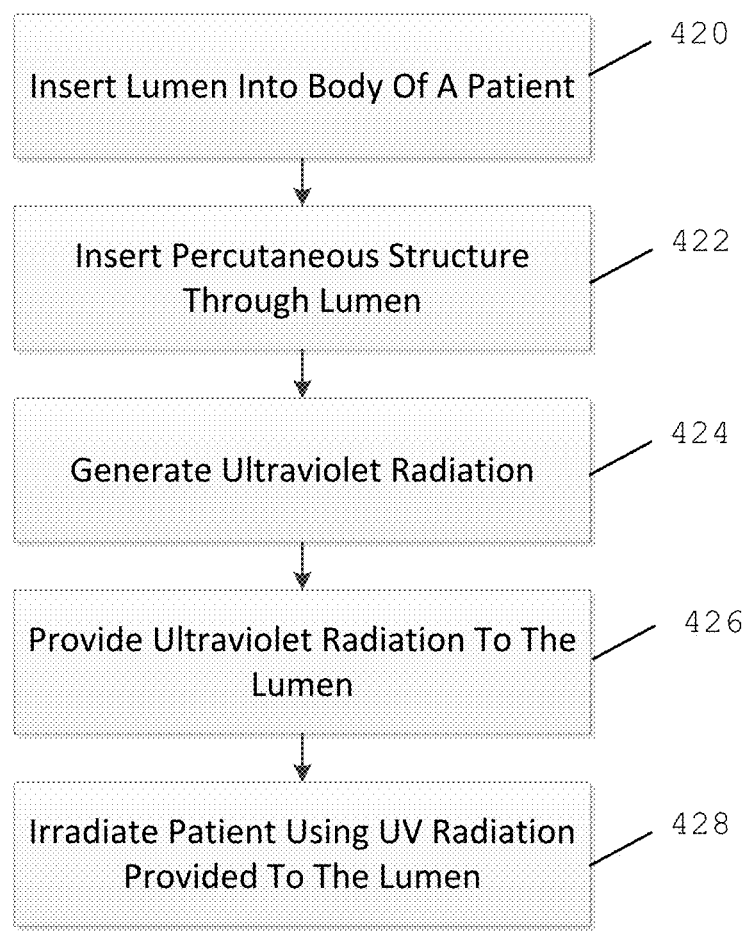
FIG. 4B is a flow chart that illustrates an exemplary method for preventing infection of a patient according to an exemplary embodiment of the present disclosure.

FIG. 4B illustrates a flow chart that illustrates an exemplary method for preventing infection of a patient according to an exemplary embodiment of the present disclosure. For example, at procedure 420, a lumen can be inserted into the body of a patient. At procedure 422, if a percutaneous structure is not integrated into the lumen, then a percutaneous structure can be inserted into the lumen. At procedure 424, ultraviolet radiation can be generated, which can be provided to the lumen at procedure 426. At procedure 428, the patient can be irradiated using the ultraviolet radiation provided to the lumen in order to prevent infection of the patient.

Figure 5A:
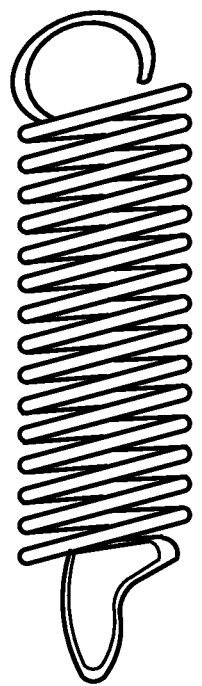
FIG. 5A is a photograph that illustrates an exemplary spiral shape of a spring, used as a shape for an optical fiber, according to an exemplary embodiment of the present disclosure.

Various alternative exemplary embodiments of the present disclosure are depicted in the following figures. FIG. 5A shows an exemplary photograph that illustrates an exemplary spiral shape of a spring, used as a shape for an optical fiber according to an exemplary embodiment of the present disclosure. This can be a spiral configuration with an angle that can leave gaps between windings that can be emulated by one or more parallel optical fibers in various exemplary embodiments. This can be less expensive, and simpler to manufacture, than the finger trap weave, but can be more difficult to fit precisely. Adhesives can be used in some embodiments. Alternate fibers can fill the gaps in the windings of an individual fiber. Such a multiple strand embodiment can be used to match the redundancy of the finger trap weave embodiment.

In some exemplary embodiments of the present disclosure, for both the parallel fibers and the finger trap weave, among others, longitudinally heterogeneous fibers, with segments alternately optimized for conduction or leakage can facilitate the correct balance of transmission and leakage over the full length of the fiber. Removing or omitting cladding at regular intervals can achieve this heterogeneity.

Figure 5B:
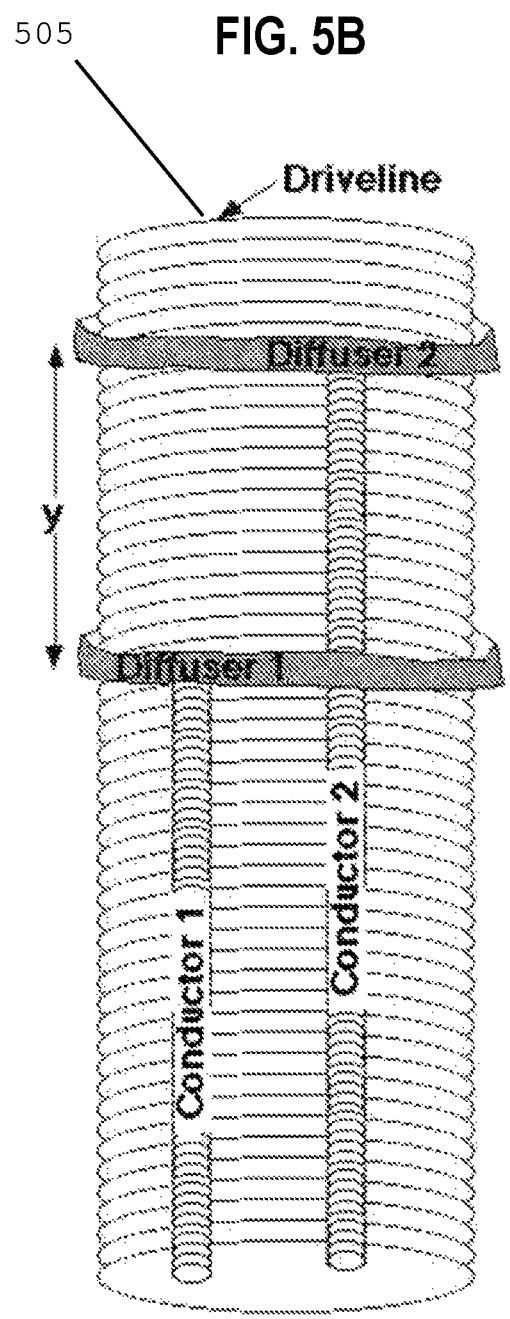
FIG. 5B is a diagram that illustrates an exemplary sleeve with two classes of fibers according to an exemplary embodiment of the present disclosure.

FIG. 5B shows an exemplary diagram that illustrates an exemplary sleeve with two classes of fibers, an exemplary to another exemplary embodiment of the present disclosure. One class of fiber can conduct the UV light with low loss to a ring made of the second class of optical fiber with high loss and diffusion of the UV light. In the exemplary embodiment, the first class can run axially along the sleeve and the second class can form a ring. The rings of the second class can be spaced a distance apart (y), such that UV light penetrates tissue a distance (y/2). Thus, the two rings (y) can illuminate all the intervening tissue. In some exemplary embodiments of the present disclosure, one or both classes of optical fibers can spiral around the sleeve, for example, with a spiral shape as shown in FIG. 5A. In some exemplary embodiments of the present disclosure, an array of six optical fibers can be arranged at regular intervals around the driveline 505, and can be parallel to its long axis. This can be simple and inexpensive to manufacture but can leave gaps in the longitudinal cytotoxic barrier if the distance y can be too great.

Figure 7A:
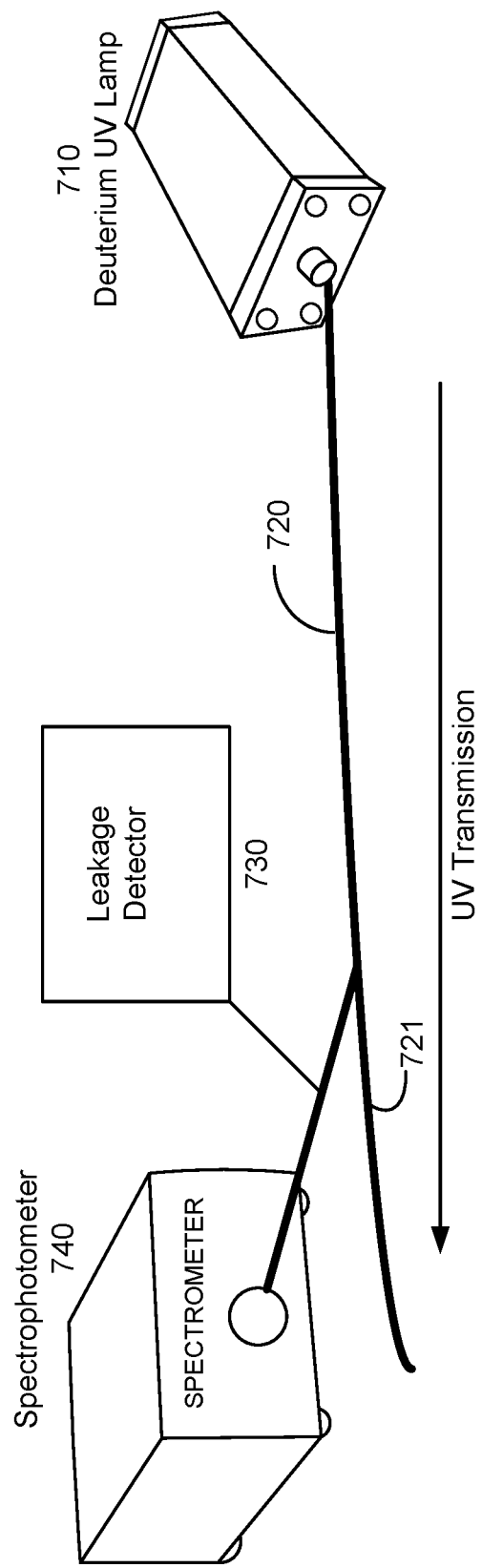
FIGS. 7A and 7B are diagrams that illustrate an exemplary experimental setup to monitor diffusion of ultraviolet light from an example optical fiber according to an exemplary embodiment of the present disclosure.
Figure 7B:
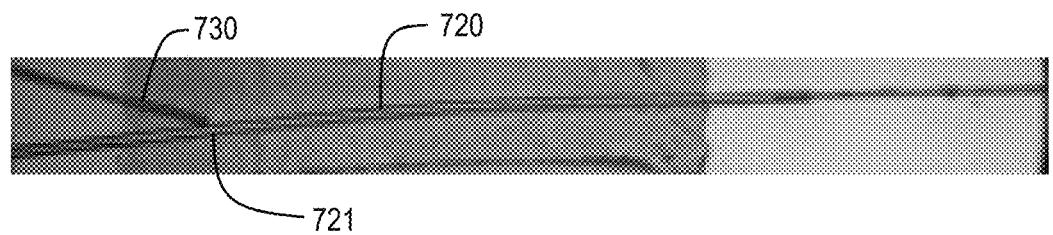

FIGS. 7A and 7B show exemplary diagrams that illustrate an exemplary experimental setup to monitor diffusion of ultraviolet light from an example optical fiber, according to an exemplary embodiment of the present disclosure. For example, the light source 710 can be a deuterium UV lamp that can be coupled into UV optical fiber 720 of water-filled TeflonAF 200 micron tubing. The light reaching a spot 721 along the optical fiber 720 can be detected by a leakage detector line 730 that can feed a spectrophotometer 740.

Figure 7C:
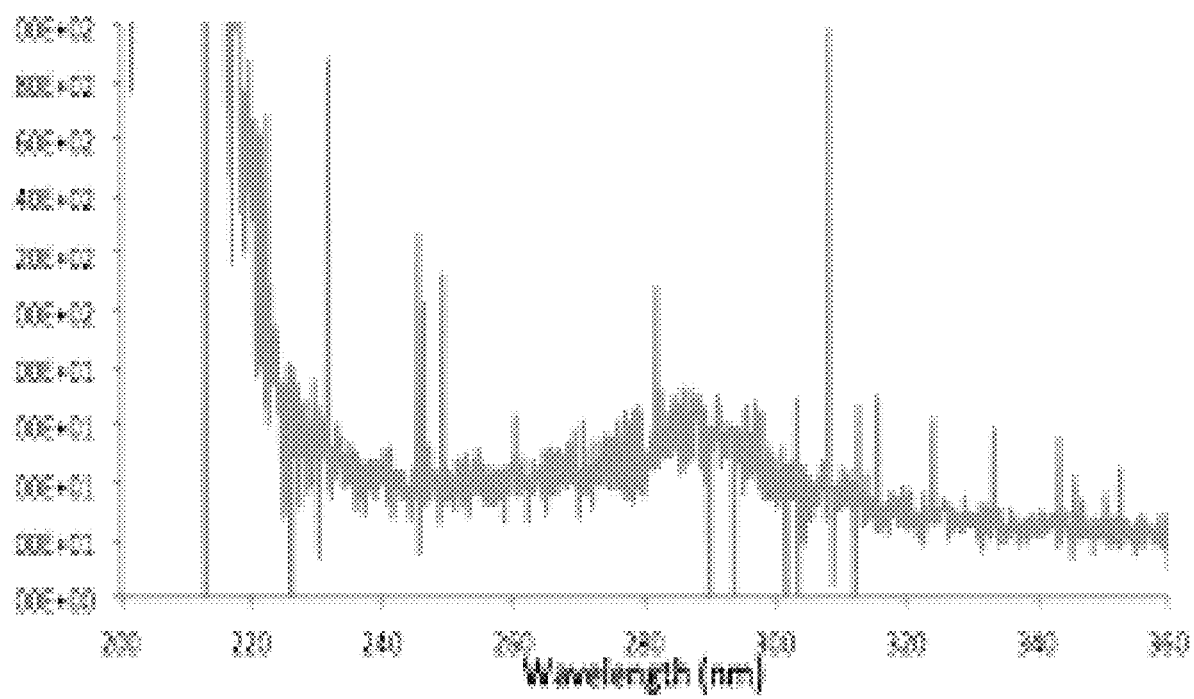
FIG. 7C is a graph that illustrates exemplary diffusion of light from an exemplary optical fiber according to an exemplary embodiment of the present disclosure.

FIG. 7C shows an exemplary graph that illustrates an exemplary diffusion of light from an exemplary optical fiber, according to an exemplary embodiment of the present disclosure. The horizontal axis indicates optical wavelength in nanometers. The vertical axis indicates light emitted in relative units (e.g., dimensionless). As can be seen, relatively little light leaks out at wavelengths above about 225 nm, while UV light in the range from 200 to 220 nm leaks at a high level, more than about 100 times higher than at the longer wavelengths.

Thus is described a specific, optimized device with a fiber configuration that can be malleable, weaveable, and durable with optimized transmission/radiation characteristics shown herein. In some exemplary embodiments of the present disclosure, a process for optimizing such devices can include a bench top component, using the apparatus shown in FIG. 7A, in which the angle of the detector tube with the optical fiber can be an informative measure. This can be used to select the best fiber conduction/radiation properties of the available optical fibers. The leakage rates along the assembled device can be confirmed to can be bactericidal. (See e.g., Reference 1).

Exemplary Controller Hardware Overview

Figure 8:
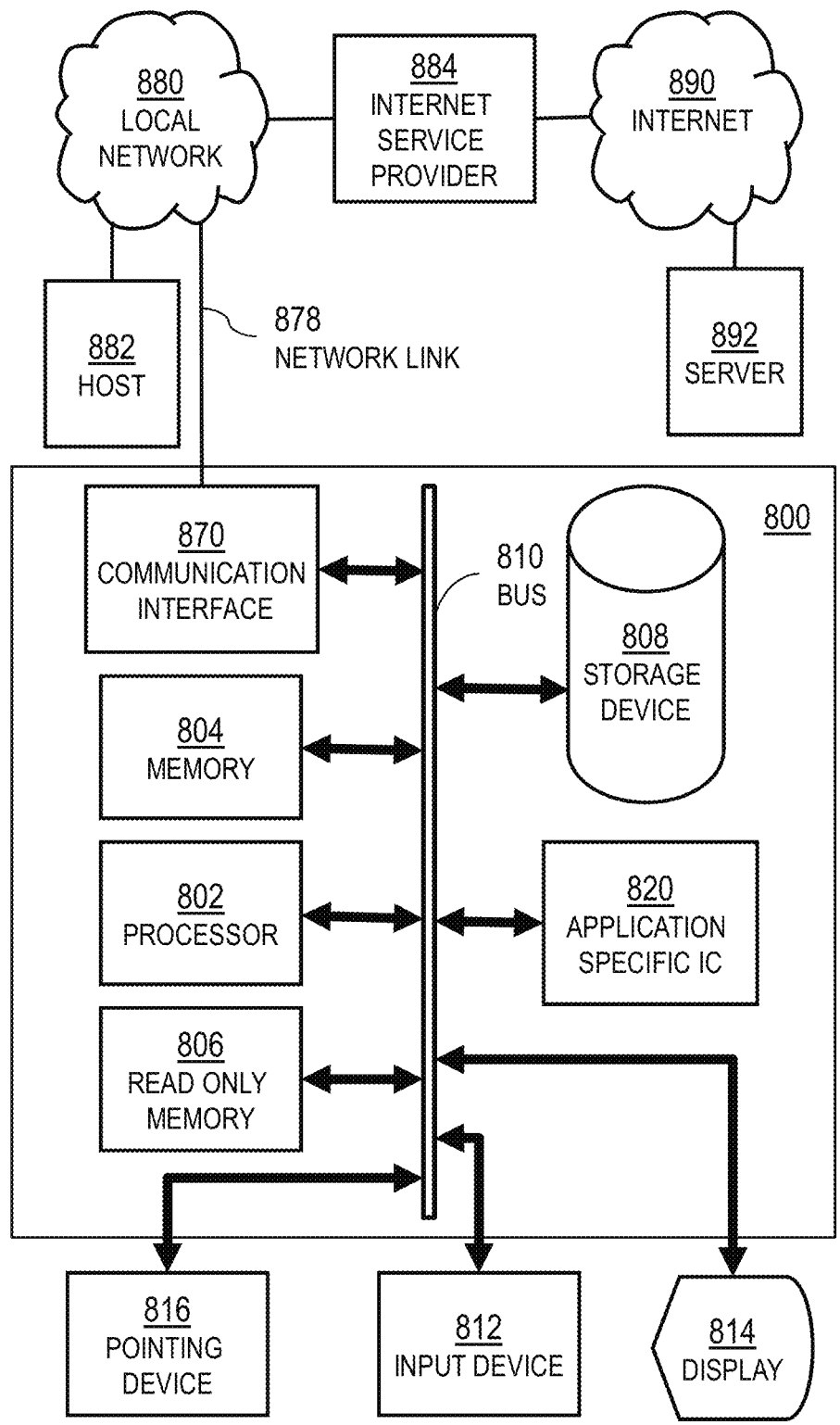
FIG. 8 is a block diagram that illustrates an exemplary computer system according to an exemplary embodiment of the present disclosure.

FIG. 8 illustrates an exemplary block diagram that illustrates a computer system 800 using which an exemplary embodiment of the present disclosure can be implemented. The exemplary computer system 800 can include a communication mechanism such as a bus 810 for passing information between other internal and external components of the computer system 800. Information can be represented as physical signals of a measurable phenomenon, typically electric voltages, but including, in other exemplary embodiments of the present disclosure, such phenomena as magnetic, electromagnetic, pressure, chemical, molecular atomic and quantum interactions. For example, north and south magnetic fields, or a zero and non-zero electric voltage, represent two states (0, 1) of a binary digit ("bit"). Other phenomena can represent digits of a higher base. A superposition of multiple simultaneous quantum states before measurement represents a quantum bit ("qubit"). A sequence of one or more digits constitutes digital data that can be used to represent a number or code for a character. In some exemplary embodiments of the present disclosure, information called analog data can be represented by a near continuum of measurable values within a particular range. Computer system 800, or a portion thereof, can perform one or more procedures of one or more methods described herein.

A sequence of binary digits constitutes digital data can be used to represent a number or code for a character. A bus 810 can include many parallel conductors of information so that information can be transferred quickly among devices coupled to the bus 810. One or more processors 802 for processing information can be coupled with the bus 810. A processor 802 can perform a set of operations on information. The set of operations can include bringing information in from the bus 810 and placing information on the bus 810. The set of operations can also typically include comparing two or more units of information, shifting positions of units of information, and combining two or more units of information, such as by addition or multiplication. A sequence of operations to be executed by the processor 802 constitutes computer instructions.

The exemplary computer system 800 can also include a memory configuration 804 coupled to the bus 810. The memory configuration 804, such as a random access memory ("RAM") or other dynamic storage device, stores information including computer instructions. Dynamic memory can facilitate information stored therein to be changed by the computer system 800. RAM can facilitate a unit of information stored at a location called a memory address to be stored and retrieved independently of information at neighboring addresses. The memory configuration 804 can also be used by a processor 802 to store temporary values during execution of computer instructions. The computer system 800 can also include a read only memory ("ROM") 806 or other static storage device coupled to the bus 810 for storing static information, including instructions that may not be changed by the computer system 800. Also coupled to the bus 810 can be or include a non-volatile ("persistent") storage device 808, such as a magnetic disk or optical disk, for storing information, including instructions, that can persist even when the computer system 800 can be turned off or otherwise loses power.

Information, including instructions, can be provided to the bus 810 for use by the processor from an external input device 812, such as a keyboard containing alphanumeric keys operated by a human user, or a sensor. A sensor can detect conditions in its vicinity and transforms those detections into signals compatible with the signals used to represent information in computer system 800. Other external devices coupled to the bus 810, for example, used primarily for interacting with users or targets, can include a display device 814, such as, for example, a cathode ray tube ("CRT"), a personal computing device ("PCD") or a liquid crystal display ("LCD"), for presenting images, and a pointing device 816, such as a mouse or a trackball or cursor direction keys, for controlling a position of a small cursor image presented on the display 814 and issuing commands associated with graphical elements presented on the display 814.

In the exemplary embodiment according to the present disclosure, special purpose hardware, such as an application specific integrated circuit ("IC") 820, can be coupled to the bus 810. The special purpose hardware can be configured to perform operations not performed by processor 802 quickly enough for special purposes. Examples of application specific ICs can include graphics accelerator cards for generating images for the display 814, cryptographic boards for encrypting and decrypting messages sent over a network, speech recognition, and interfaces to special external devices, such as robotic arms and medical scanning equipment that repeatedly perform some complex sequence of operations that can be more efficiently implemented in hardware.

The exemplary computer system 800 can also include one or more instances of a communications interface 870 coupled to the bus 810. Communication interface 870 can provide a two-way communication coupling to a variety of external devices that can operate with their own processors, such as printers, scanners and external disks. The coupling can be with a network link 878 that can be connected to a local network 880, to which a variety of external devices with their own processors can be connected. For example, the communication interface 870 can be a parallel port or a serial port or a universal serial bus ("USB") port on a personal computer. In some exemplary embodiments of the present disclosure, the communications interface 870 can be an integrated services digital network ("ISDN") card or a digital subscriber line ("DSL") card or a telephone modem that provides an information communication connection to a corresponding type of telephone line.

In some embodiments, the communication interface 870 can be or include a cable modem that converts signals on the bus 810 into signals for a communication connection over a coaxial cable or into optical signals for a communication connection over a fiber optic cable. As another example, the communications interface 870 can be a local area network ("LAN") card to provide a data communication connection to a compatible LAN, such as Ethernet. Wireless links can also be implemented. Carrier waves, such as acoustic waves and electromagnetic waves, including radio, optical and infrared waves can travel through space without wires or cables. Signals can include man-made variations in amplitude, frequency, phase, polarization or other physical properties of carrier waves. For wireless links, the communications interface 870 can send and receive electrical, acoustic or electromagnetic signals, including infrared and optical signals that carry information streams, such as digital data.

The term computer-readable medium can be used herein to refer to any medium that participates in providing information to the processor 802, including instructions for execution. Such a medium can take many forms, including, but not limited to, non-volatile media, volatile media and transmission media. Non-volatile media can include, for example, optical or magnetic disks, such as the storage device 808. Volatile media can include, for example, the dynamic memory 804. Transmission media can include, for example, coaxial cables, copper wire, fiber optic cables and waves that travel through space without wires or cables, such as acoustic waves and electromagnetic waves, including radio, optical and infrared waves. The term computer-readable storage medium can be used herein to refer to any medium that participates in providing information to the processor 802, except for transmission media.

Common forms of computer-readable media can include, for example, a floppy disk, a flexible disk, a hard disk, a magnetic tape, or any other magnetic medium, a compact disk ROM ("CD-ROM"), a digital video disk ("DVD") or any other optical medium, punch cards, paper tape, or any other physical medium with patterns of holes, a RAM, a programmable ROM ("PROM"), an erasable PROM ("EPROM"), a FLASH-EPROM, or any other memory chip or cartridge, a carrier wave, or any other medium from which a computer can read. The term non-transitory computer-readable storage medium can be used herein to refer to any medium that can participate in providing information to processor 802, except for carrier waves and other signals.

Logic encoded in one or more tangible media can include one or both of processor instructions on a computer-readable storage media and special purpose hardware, such as ASIC 820.

A network link 878 can provide information communication through one or more networks to other devices that use or process the information. For example, network link 878 can provide a connection through the local network 880 to a host computer 882 or to equipment 884 operated by an Internet Service Provider ("ISP"). The ISP equipment 884 in turn can provide data communication services through the public, world-wide packet-switching communication network of networks now commonly referred to as the Internet 890. A computer called a server 892 connected to the Internet can provide a service in response to information received over the Internet. For example, the server 892 can provide information representing video data for presentation at the display 814.

The exemplary computer system 800 is provided for implementing the techniques described herein. According to an exemplary embodiment of the present disclosure, those procedures can be performed by the computer system 800 in response to the processor 802 executing one or more sequences of one or more instructions contained in the memory 804. Such instructions, also called software and program code, can be read into the memory 804 from another computer-readable medium, such as the storage device 808. Execution of the sequences of instructions contained in the memory 804 can cause processor 802 to perform the method/procedures described herein. In some exemplary embodiments of the present disclosure, hardware, such as the application specific integrated circuit 820, can be used in place of or in combination with software to implement the invention. Thus, exemplary embodiments of the present disclosure are not limited to any specific combination of hardware and software.

The signals transmitted over the network link 878 and other networks through the communications interface 870, can carry information to and from the computer system 800. The exemplary computer system 800 can send and receive information, including program code, through the networks 880, 890 among others, through network link 878 and through communications interface 870. In an example using the Internet 890, a server 892 can transmit program code for a particular application, requested by a message sent from the computer 800, through Internet 890, ISP equipment 884, local network 880 and communications interface 870. The received code can be executed by the processor 802 as it can be received, or it can be stored in storage device 808 or other non-volatile storage for later execution, or both. In this manner, the computer system 800 can apply program code in the form of a signal on a carrier wave.

Various forms of computer readable media can be involved in carrying one or more sequence of instructions or data or both to the processor 802 for execution. For example, instructions and data can initially be carried on a magnetic disk of a remote computer such as the host 882. The remote computer can load the instructions and data into its dynamic memory and can send the instructions and data over a telephone line using a modem. A modem local to the computer system 800 can receive the instructions and data on a telephone line and uses an infra-red transmitter to convert the instructions and data to a signal on an infra-red a carrier wave serving as the network link 878. An infrared detector serving as the communications interface 870 can receive the instructions and data carried in the infrared signal and place information representing the instructions and data onto the bus 810. The bus 810 can carry the information to memory 804, from which processor 802, can retrieve and execute the instructions using some of the data sent with the instructions. The instructions and data received in memory 804 can optionally be stored on storage device 808, either before or after execution by the processor 802.

Figure 9:
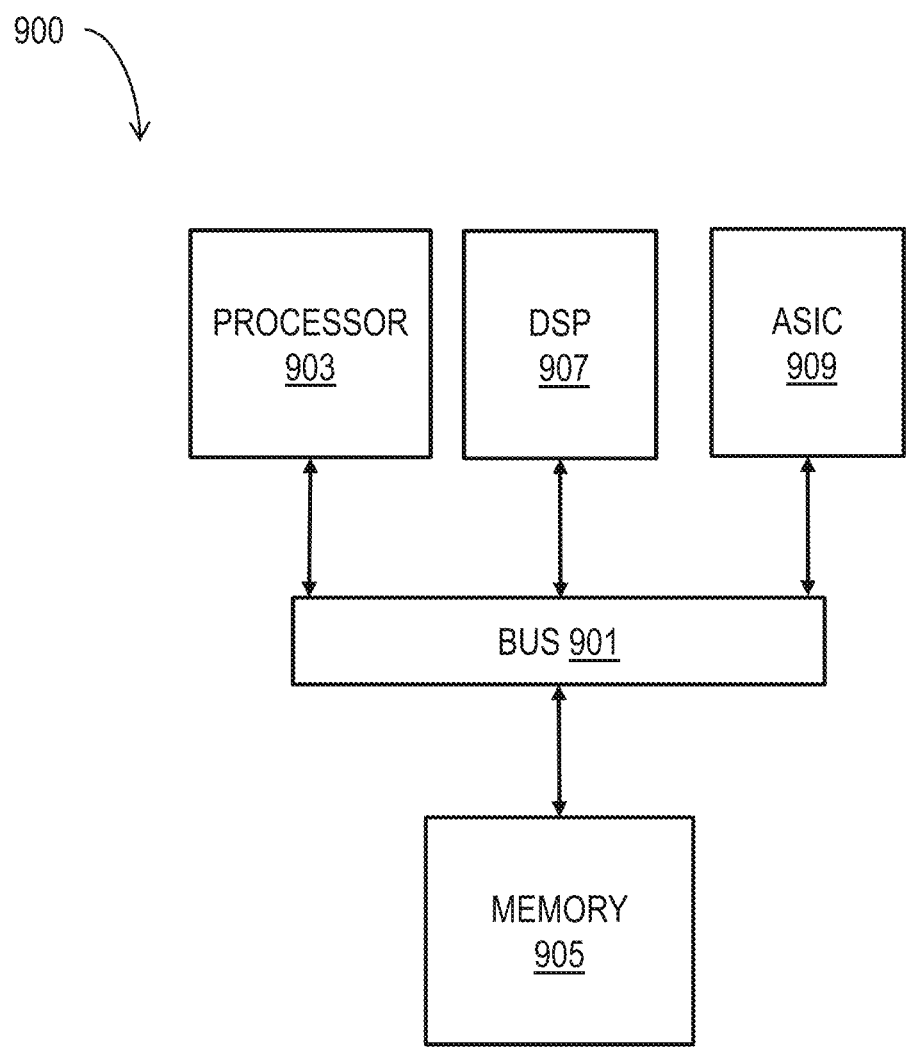
FIG. 9 is a block diagram that illustrates an exemplary hardware for use with the exemplary device, according to an exemplary embodiment of the present disclosure.

FIG. 9 illustrates an exemplary hardware configuration 900 using which an exemplary embodiment of the present disclosure can be implemented. Chip set 900 can be programmed to perform one or more procedures of a method described herein and can include, for instance, the processor and memory components described herein with respect to FIG. 8 incorporated in one or more physical packages or configurations (e.g., chips). By way of example, a physical package can include an arrangement of one or more materials, components and/or wires on a structural assembly (e.g., a baseboard) to provide one or more characteristics such as physical strength, conservation of size, and/or limitation of electrical interaction. It can be contemplated that in certain exemplary embodiments of the present disclosure the chip set can be implemented in a single chip. Chip set 900, or a portion thereof, can be used to perform one or more procedures of a method described herein.

In some exemplary embodiment of the present disclosure, the chip set 900 can include a communication mechanism such as a bus 901 for passing information among the components of the chip set 900. A processor 903 can be connected to the bus 901 to execute instructions and process information stored in, for example, a memory 905. The processor 903 can include one or more processing cores with each core configured to perform independently. A multi-core processor enables multiprocessing within a single physical package. Examples of a multi-core processor include two, four, eight or a greater numbers of processing cores. Alternatively, or in addition, the processor 903 can include one or more microprocessors configured in tandem via the bus 901 to enable independent execution of instructions, pipelining, and multithreading. The processor 903 can also be accompanied with one or more specialized components to perform certain processing functions and tasks such as one or more digital signal processors ("DSP") 907, or one or more application-specific integrated circuits ("ASIC") 909. A DSP 907 typically can be configured to process real-world signals (e.g., sound) in real time independently of the processor 903. Similarly, an ASIC 909 can be configured to performed specialized functions not easily performed by a general purposed processor. Other specialized components to aid in performing the inventive functions described herein include one or more field programmable gate arrays ("FPGA"), one or more controllers, or one or more other special-purpose computer chips.

The processor 903 and accompanying components have connectivity to the memory 905 via the bus 901. The memory 905 includes both dynamic memory (e.g., RAM, magnetic disk, writable optical disk, etc.) and static memory (e.g., ROM, CD-ROM, etc.) for storing executable instructions that when executed perform one or more procedures of a method described herein. The memory 905 also stores the data associated with or generated by the execution of one or more procedures of the methods described herein.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety:
1. Buonanno M., Randers-Pehrson G., Bigelow A. W., Trivedi S., Lowy F. D., Spotnitz H. M., Hammer S. M., Brenner D. J.; 207-nm UV light—a promising tool for safe low-cost reduction of surgical site infections. I: in vitro studies. PLoS One. 2013 Oct. 16; 8(10):e76968.
2. Randers-Pehrson, G., Brenner D. J., Brenner D. J, Bigelow A. W., Apparatus, Method, and System for Selectively Affecting and/or Killing Bacteria, World Intellectual Property Organization, WO2012/122210 A1, 13 Sep. 2012

What is claimed is:
1. An ultraviolet (UV) arrangement, comprising:
a lumen structured to be inserted into a body of a patient and pass a percutaneous structure therethrough into the body of the patient;
fibers embedded in the lumen, wherein the fibers are configured to disperse or provide a UV radiation externally from the UV arrangement; and
an optical arrangement coupled to the fibers, and configured to generate the UV radiation, and provide the UV radiation to the fibers to be dispersed or provided by the fibers,
wherein the optical arrangement includes a plurality of diffusing rings, and wherein each ring is connected to one of the fibers.
2. The UV arrangement of claim 1, wherein the fibers are shaped as a weave.
3. The UV arrangement according to claim 1, wherein the percutaneous structure is integrated into the lumen.
4. The UV arrangement of claim 1, wherein an outer surface of the lumen is composed of Polytetrafluoroethylene.
5. The UV arrangement of claim 1, wherein the optical arrangement includes at least one laser.
6. The UV arrangement of claim 1, further comprising at least one portable power source configured to power at least one of the optical arrangement or the percutaneous structure.
7. The UV arrangement of claim 1, further comprising at least one anchor configured to attach the lumen to a skin of the patient.
8. The UV arrangement of claim 1, further comprising at least one anchor configured to attach the lumen to the percutaneous structure.
9. The UV arrangement of claim 1, wherein a wavelength of the UV radiation is in range of about 190 nanometers to about 230 nanometers.
10. An ultraviolet (UV) arrangement, comprising:
a lumen structured to be inserted into a body of a patient and pass a percutaneous structure therethrough into the body of the patient;
fibers embedded in the lumen, wherein the fibers are configured to disperse or provide a UV radiation externally from the UV arrangement; and
an optical arrangement coupled to the fibers, and configured to generate the UV radiation, and provide the UV radiation to the fibers to be dispersed or provided by the fibers,
wherein the percutaneous structure is integrated into the lumen, and wherein the percutaneous structure is a driveline for a left ventricular assist device.
11. An ultraviolet (UV) arrangement, comprising:
a lumen structured to be inserted into a body of a patient and pass a percutaneous structure therethrough into the body of the patient;
fibers embedded in the lumen, wherein the fibers are configured to disperse or provide a UV radiation externally from the UV arrangement; and
an optical arrangement coupled to the fibers, and configured to generate the UV radiation, and provide the UV radiation to the fibers to be dispersed or provided by the fibers, wherein a power level of the UV radiation is at least about 0.04 milliWatts per centimeter squared of an area of an outer surface of the lumen.
12. A method for preventing infection of a patient, comprising:
inserting a lumen into a body of the patient;
inserting a percutaneous structure through the lumen into the body of the patient;

coupling an optical arrangement to fibers embedded in an outer surface of the lumen;
generating an Ultraviolet (UV) radiation using the optical arrangement;
providing the UV radiation to the fibers to disperse or provide the UV radiation from the lumen into the body of the patient; and
irradiating the patient using the UV radiation provided to the fibers, wherein the optical arrangement includes a plurality of diffusing rings, and wherein each ring is connected to one of the fibers.

13. The method of claim 12, wherein a wavelength of the UV radiation is in a range of about 190 nanometers to about 230 nanometers.

14. The method of claim 12, wherein the fibers are shaped as a weave.

15. The method of claim 14, wherein the UV radiation is generated using a laser.

16. A method for preventing infection of a patient, comprising: inserting a lumen into a body of the patient;
coupling an optical arrangement to fibers embedded in an outer surface of the lumen;
inserting a percutaneous structure through the lumen into the body of the patient;
generating an ultraviolet (UV) radiation using the optical arrangement;
providing the UV radiation to the fibers to disperse or provide the UV radiation from the lumen into the body of the patient; and
irradiating the patient using the UV radiation provided to the fibers,
wherein the percutaneous structure is integrated into the lumen, and wherein the percutaneous structure is a driveline for a left ventricular assist device.

17. A method for preventing infection of a patient, comprising:
inserting a lumen into a body of the patient;
inserting a percutaneous structure through the lumen into the body of the patient;
coupling an optical arrangement to fibers embedded in an outer surface of the lumen;
generating an ultraviolet (UV) radiation using the optical arrangement;
providing the UV radiation to the fibers to disperse or provide the UV radiation from the lumen into the body of the patient; and
irradiating the patient using the UV radiation provided to the fibers,
wherein a power level of the UV radiation is at least about 0.04 milliWatts per centimeter squared of an area of an outer surface of the lumen.

* * * * *